(12) United States Patent
Osmundson et al.

(10) Patent No.: US 8,335,364 B2
(45) Date of Patent: Dec. 18, 2012

(54) ANATOMY LABELING

(75) Inventors: Sarah Osmundson, St. Louis Park, MN (US); Wade J. Steigauf, Bloomington, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 477 days.

(21) Appl. No.: 12/722,233

(22) Filed: Mar. 11, 2010

(65) Prior Publication Data

US 2011/0225530 A1    Sep. 15, 2011

(51) Int. Cl.
*G06K 9/00* (2006.01)

(52) U.S. Cl. ........................ 382/128; 382/291

(58) Field of Classification Search .................. 392/128, 392/131, 132, 291, 311; 128/922
See application file for complete search history.

(56) References Cited

U.S. PATENT DOCUMENTS

| | | | |
|---|---|---|---|
| 2008/0117225 A1* | 5/2008 | Wegenkittl et al. | 345/581 |
| 2010/0135554 A1* | 6/2010 | Kohlmann et al. | 382/128 |
| 2010/0275145 A1* | 10/2010 | Nijlunsing et al. | 715/769 |

* cited by examiner

*Primary Examiner* — Andrew W Johns
(74) *Attorney, Agent, or Firm* — Schwegman Lundberg & Woessner P.A.

(57) ABSTRACT

In one example, a two points on a medical image can be identified. In this example, three or more anatomical features can be identified and labeled. For example, these labels can be displayed with other medical images that show the same anatomical features. For example, points in the L1 and L5 vertebrae can be identified, and labels for the L1-L5 vertebrae can be displayed.

20 Claims, 6 Drawing Sheets

ANATOMY LABELING

BACKGROUND

Medical images, such as X-rays, CAT (computerized axial tomography) scans, and MRI's (Magnetic Resonance Imaging), may be digitized to facilitate remote reading by radiologists. A hospital or other medical facility may use machines that capture and digitize the images and transmit them to a remote image server, such as a Picture Archiving and Communications System (PACS). The transmission may occur over a network, such as an intranet or the Internet.

Additionally, the hospital may also transmit orders corresponding to the images to an order server, such as a Radiologist Information System (RIS). The orders may be requests for a radiologist to interpret, or read, the images and return a diagnostic report. Orders may also contain information, such as a patient identifier, the procedure type associated with the image, patient demographic information, and a hospital identifier.

Both the images and orders may be transmitted by the image server and the order server, respectively, to a remote system operated by a radiologist. After receipt of the images and orders, the radiologist may analyze the image and return the diagnostic report using the remote system. The diagnostic report may be transmitted through the network to the order server, which may send the report to the hospital or other medical facility that originally transmitted the order and images corresponding to the report.

SUMMARY

In one example, a two points on a medical image can be identified. In this example, three or more anatomical features can be identified and labeled. For example, these labels can be displayed with other medical images that show the same anatomical features. For example, points in the L1 and L5 vertebrae can be identified, and labels for the L1-L5 vertebrae can be displayed.

In another example, graphical user interface displays a medical image with anatomical features. In this example, user input can identify the location of two points on the medical image. The graphical user interface, for example, can show three or more labels in response to the user input.

In a further example, a teleradiology system can capture a medical image, display the image to a user, and receive an indication of the location of two features. Three or more labels can be associated with the image, and stored for display on a user terminal.

The details of one or more implementations are set forth in the accompanying drawing and description below. Other features, objects, and advantages will be apparent from the description and drawings, and from the claims.

DESCRIPTION OF DRAWINGS

Like reference symbols in various drawing indicate like elements.

DETAILED DESCRIPTION OF ILLUSTRATIVE IMPLEMENTATIONS

Illustrative implementations of computer-based systems, methods, and interfaces for generating, displaying, and adjusting radiological images are described. The described systems, methods, and interfaces can enable a radiologist in a teleradiology environment to view, interact with, and analyze images, and to provide diagnostic findings to a medical facility.

Figure 1:
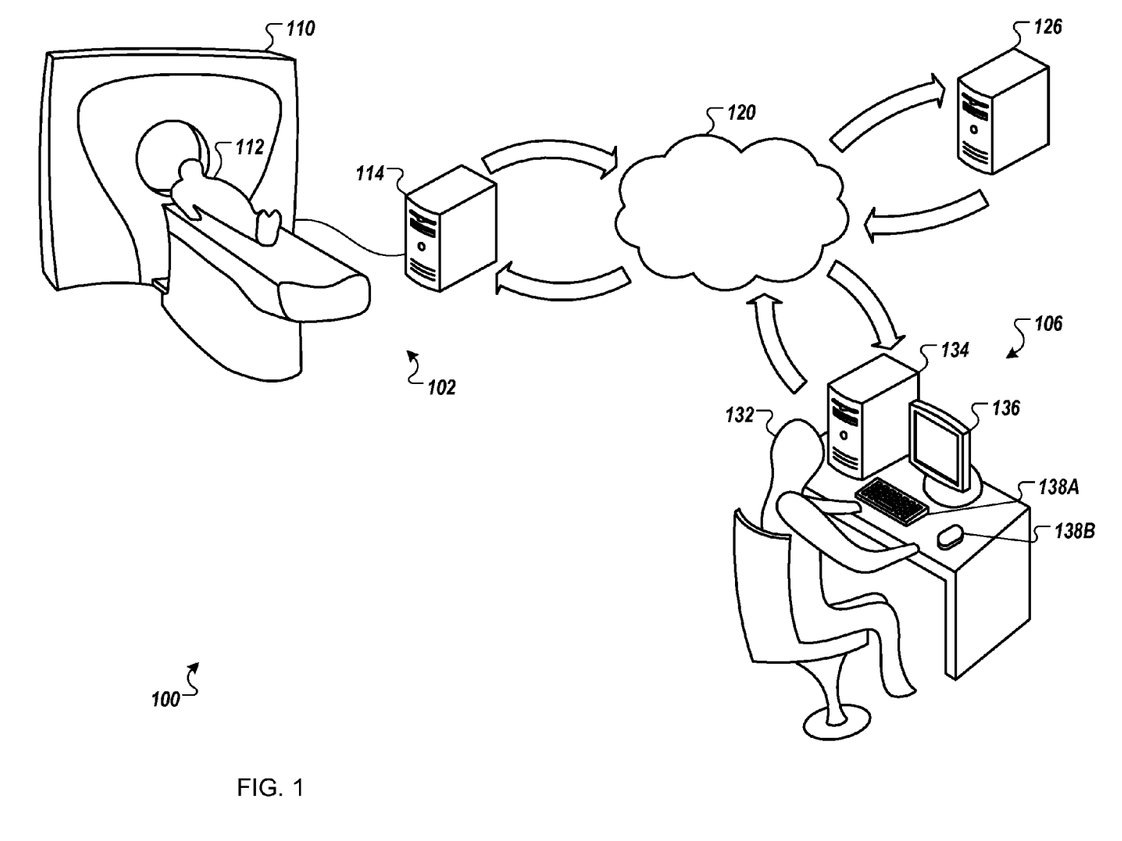
FIG. 1 shows an example system.

Referring to FIG. 1, an example teleradiology system 100 is shown. The system 100 can be used for capturing medical image data in one location and for reviewing medical images associated with the data in another location. The system 100 can include many geographically separated imaging devices and many image review terminals. For purposes of illustration, the teleradiology system 100 shown in FIG. 1 includes an imaging system 102, an image order (IO) management system 104, and an image review system 106. The imaging system 102, for example, may include an imaging device 110, such as a CT (computer tomography) scanner or an MRI (magnetic resonance imaging) scanner. Using an energy source such as x-rays or magnetic fields, for example, the imaging device 110 may capture image data associated with a subject 112 (e.g., a patient). In some implementations, the image data may include a series of two-dimensional images. In some implementations, the image data may be used to produce a three-dimensional model that can be further manipulated and reformatted for generating two-dimensional (or three-dimensional) images. Image data captured by the imaging device 110 can be stored and processed by an imaging device server 114 (e.g., one or more computers with a processor and a memory) and can be provided to other systems and computers in the system 100 through a network 120 (e.g. an intranet or the Internet).

In some implementations, image data may be provided to the IO management system 104, where the data may be stored and processed by one or more computers. For example, the IO management system 104 may determine that the image data is to be provided to a system user 132 (e.g., a radiologist) at the image review system 106. As shown, image data can be provided by the IO management system 104 to the image review system 106 through the network 120.

The image review system 106, for example, may include an image display server 134 (e.g., one or more computers with a processor and a memory), a display device 136 (e.g., a monitor), and input devices 138A-B (e.g., keyboards, computer mice, joysticks, touch interfaces, voice interfaces, and the like). In some implementations, image data may be processed by the image display server 134 and visually presented to the user 132 as one or more images at the display device 136. Using the input devices 138A-B, the user 132 may interact with the presented images, for example, by manipulating one or more user controls included in a graphical user interface presented at the display device 136 in association with the images. For example, the user 132 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the user 132 may produce and indicate a diagnostic finding related to the subject 112.

Figure 2:
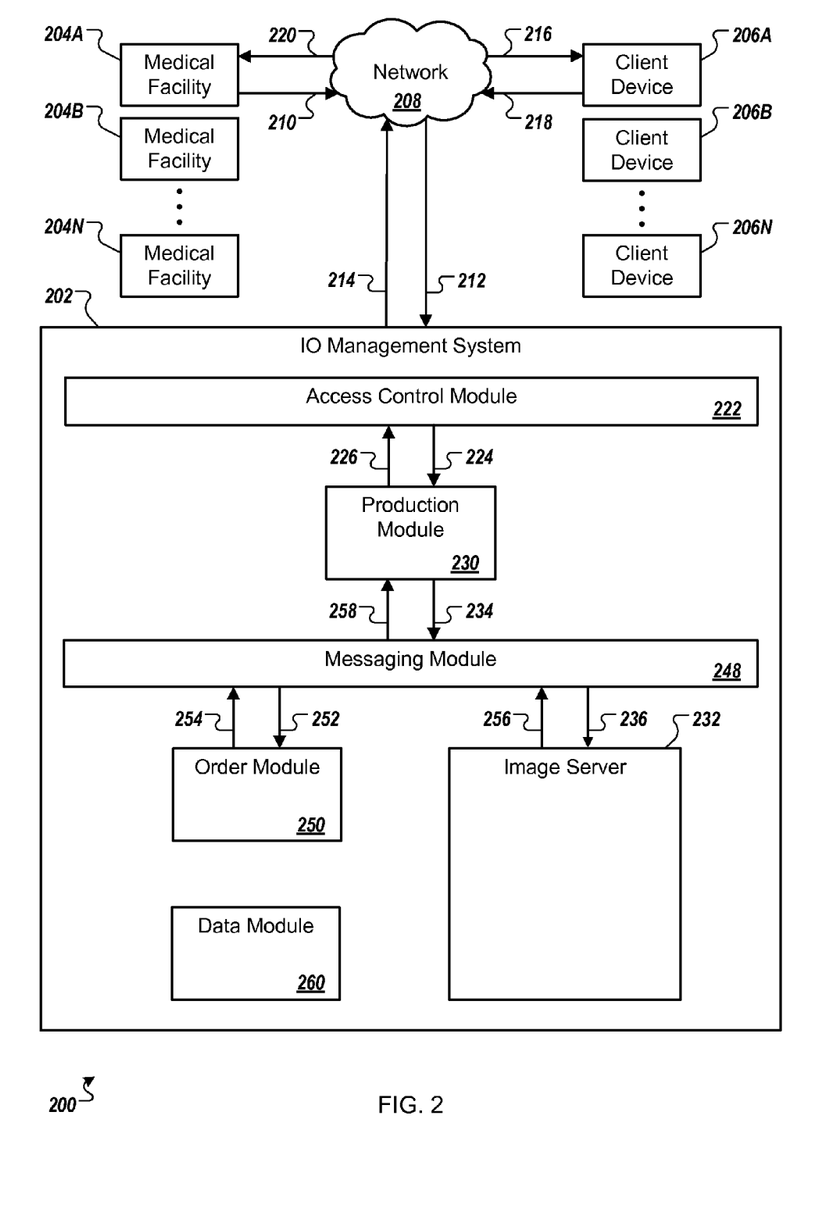
FIG. 2 is a block diagram of an example teleradiology system.

FIG. 2 shows an example of a teleradiology system 200 including an image order management system 202, medical facilities 204, and client devices 206 connected by a network 208, such as the Internet. The medical facilities 204 may send images and orders for studying the images to the IO management system 202, as represented by arrows 210 and 212. The images may include representations of body parts such as x-rays, CAT scans, and MRIs. The images may also contain information, such which medical facility sent the image, the number of images in the transmission, the patient name, and other patient demographic information. The orders may contain information about a patient, such as name, medical history, and the reason the image was taken. The order may also include a description of an associated image, such as a pelvic abdominal scan, a number of images associated with the order, and an order type, such as preliminary or final read. The presence of the patient name and other patient information may enable a particular image to be linked with a particular order. The IO management system 202 may store the images and orders and assign the orders to appropriate users at the client devices 206. For example, the IO management system 202 may assign an order from a medical facility 204A to a radiologist at a client device 206A. If the radiologist accepts the order, the IO management system 202 may make the images associated with the order available to the radiologist for viewing, as indicated by arrows 214 and 216. The radiologist can interpret the images and send a report back to the IO management system 202, as represented by arrows 218 and 212. The IO management system 202 may then forward the report to the originating medical facility, as indicated by arrows 214 and 220, where the report may be used in a diagnosis for the patient.

The IO management system 202 may be implemented on a single computing device or on multiple computing devices, such as a server farm. In some implementations, the IO management system 202 may be disbursed over several servers that are connected through a network. This configuration may enable expansion of the system and flexibility in managing the flow of received and output images and orders.

Medical facilities may send images and orders at the same time as one another or at different times. Images, orders, and reports may be sent over the same network or different networks. For example, the IO management system 202 may receive images and orders through a single T1 connection to the Internet, or the images may be received from the Internet through a T1 connection and the orders may be received through a modem connection. As another example, the IO management system 202 may receive an image and an order from a medical facility over the Internet and return a corresponding report to the medical facility over a fax connection.

Additionally, the images and orders may be sent separately or combined in one transmission. For instance, a computing device at a medical facility may use software that sends the orders and the images with a single application and single set of actions, or the medical facility may send the images using one application that sends one transmission and send the orders using a different application that sends a separate transmission.

In some implementations, the network 208 may be a secure network, such as a virtual private network (VPN). The VPN may include a secure computing device or terminal at the medical facility 204, at the IO management system 202, and at the client device 206. Encrypted transmissions (e.g., of image and order data) sent through the network 208 between the medical facility 204, the IO management system 202, and the client device 206 may also include the use of other forms of secure communications, such as the Secure Socket Layer (SSL), Terminal Services, and Citrix systems.

In the IO management system 202 there may be an access control module 222 that controls user access to the IO management system 202. Users may include staff at a hospital, imaging center, medical research facility or other medical facility and radiologists at the client devices 206. For example, the access module 222 may include a remote desktop application, such as Terminal Services, that allows users to login to the management system 202. As another example, the access control module 222 may include an application portal accessible from the remote desktop or from the Internet with individual logins and passwords for each user. If the access control module 222 grants access to a user at the medical facility 204A, the user may be able to send images and orders or receive reports, as indicated by arrows 224 and 226, respectively. If an order is assigned to and accepted by a radiologist at the client device 206A, the radiologist may be able to retrieve the order and its images or send a report. The access control module 222 may also monitor the connectivity status of the medical facilities 204 or the client devices 206. For example, control module 222 may monitor whether a secure network connection between the medical facilities 204 or the client devices 206 and the I/O management system 202 is operational.

When image data is received by the IO management system 202 and accepted by the access control module 222 it may be sent to a production module 230. The production module 230 may handle real-time processing in the IO management system 202, such as managing the workflow of orders and images. The production module 230 may forward the image data to an image server 232, as indicated by arrows 234 and 236, for processing and storage. For example, the image server 232 may be part of a Picture Archive Communication System (PACS), which may digitally store, process, transmit, and facilitate the display of radiology images.

In some implementations, the production module 230 and the image server 232 may not communicate in the same format, so a messaging module 248 may handle communications between the two. For example, if the production module 230 is able to read text files as input, the messaging module 248 may take output from another source, such as the image server 232, and convert it into a text file format that the production module 230 can interpret.

When an order is received by the IO management system 202 and accepted by the access control module 222 it may be sent to the production module 230. The production module 230 may forward the order to an order module 250, such as a Radiology Information System (RIS), as represented by arrows 234 and 252, for processing. The messaging module 248 may process communication between the production module 230 and the order module 250.

Once the IO management system 202 receives an order, the production module 230 may assign the order to a user of a client device 206. The production module 230 may also assign the order to several users at several client devices 206. If the access control module 222 grants a user of a client device access, the user may retrieve orders from the order module 250 and image data from the image server 232, as indicated by arrows 254, 256, and 258.

The IO management system 202 may include a data module 160 that stores data associated with the system 202. For example, order data used by the order module 250 and image data used by the image server 232 may be stored by the data module 160. In some implementations, image data may be stored by the image server 232.

Figure 3:
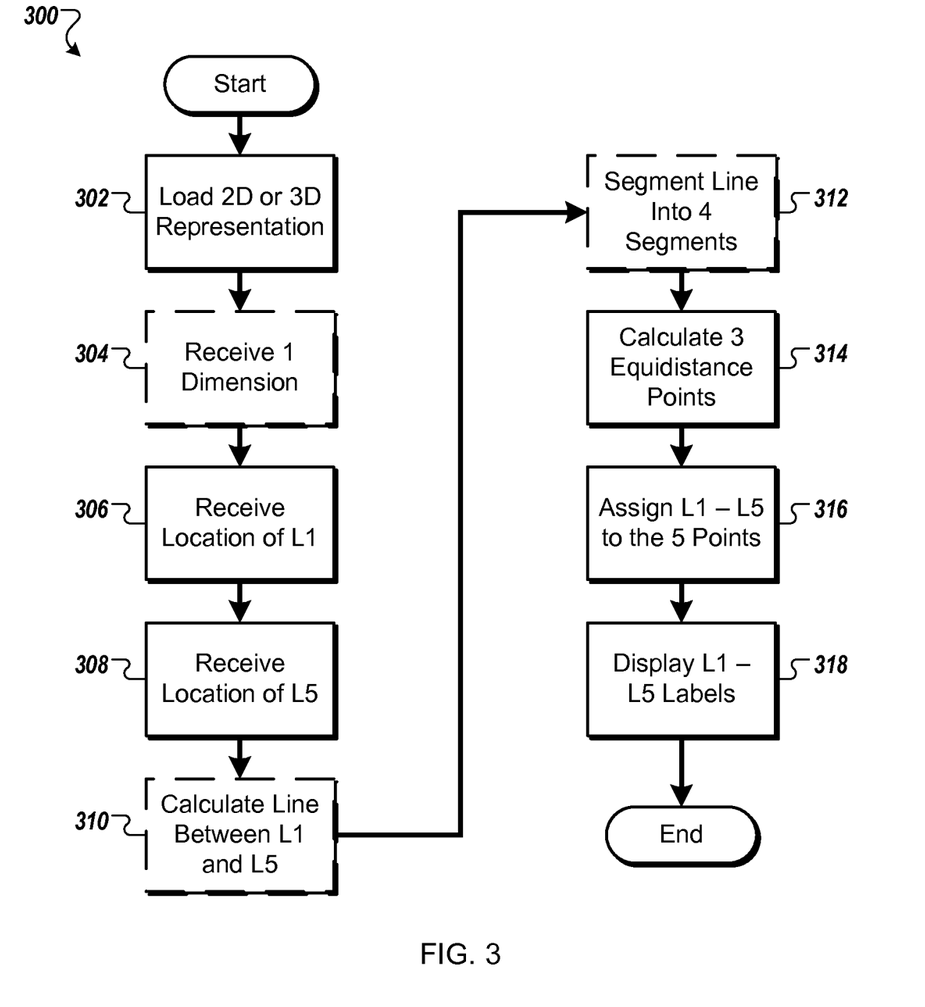
FIG. 3 is a flow chart of an example process for labeling anatomy.

FIG. 3 is a flow chart of an example process 300 for labeling anatomy. The process 300 can be performed, for example, by a computer executing a medical image analysis program which displays medial images to a user for medical review. The process 300 can receive user input and determine the location of anatomical features based on the input.

One or more two-dimensional or three-dimensional representations of a patient are loaded (302) for display to a user. The representation can be displayed as a two-dimensional image to a user. In the case of a three-dimensional image, or a series of two dimensional images representing parallel planes of view, a first dimension can be set by a user to create the two-dimensional view (304).

For purposes of illustration, the first dimension will be referred to a "Z", and the two dimensions of the image displayed to the user will be referred to as "X" and "Y". In this example, a cross-sectional view of a spine is presented to a user, and a computer mouse is being used for input, but it will be understood that views of other anatomy and/or other input methods are possible.

The user moves a cursor over a point on the image and clicks to select a location in what the user recognizes to be the L1 vertebra (306). In response, a first point is recorded with the X and Y coordinates of the cursor, and with the Z coordinate if set. The user moves the cursor and selects a location in what the user recognizes to be the L5 vertebra (308). In response, a second point is recorded with the X and Y coordinates of the cursor, and with the Z coordinate if set.

A line or line segment is calculated so that it passes through or in between the two points (310). The line or line segment is further segmented into four equal length segments between the two points (312). A third, fourth, and fifth, point are calculated (314), each at the end of two line segments.

Flags for each of the L1, L2, L3, L4 and L5 vertebrae are assigned to the respective points (316). These flags, which can contain two-dimensional or three-dimensional location data, can be displayed as labels (318). The labels can be shown in the view presented to the user for input, and/or in other views of the same anatomical area. For example, if a three dimensional representation is rotated 45° about the X and Y axis, the labels can be shown in the same position, relative to the anatomy in the image and with displayed text rotated to be readable from the new view. The labels can be changed based on the distance of the labels from the camera. For example, the labels can have reduced transparency if they are farther than a predefined or user defined distance from the camera.

Although a particular number, kind, and order of operations is shown in this example, other numbers, kinds, and orders of operations are possible. For example, the user inputs (306) and (308) can indicate points in the first and seven ribs. In this example, five additional points can be calculated, and the points can be spaced differently. In the process 300, the operations 310-318 are processed automatically after the user input in operation 308. In some examples, additional or intermediary operations including user input, such as to verify points or select the kind of anatomy tagged by the user, can occur.

Figure 4:
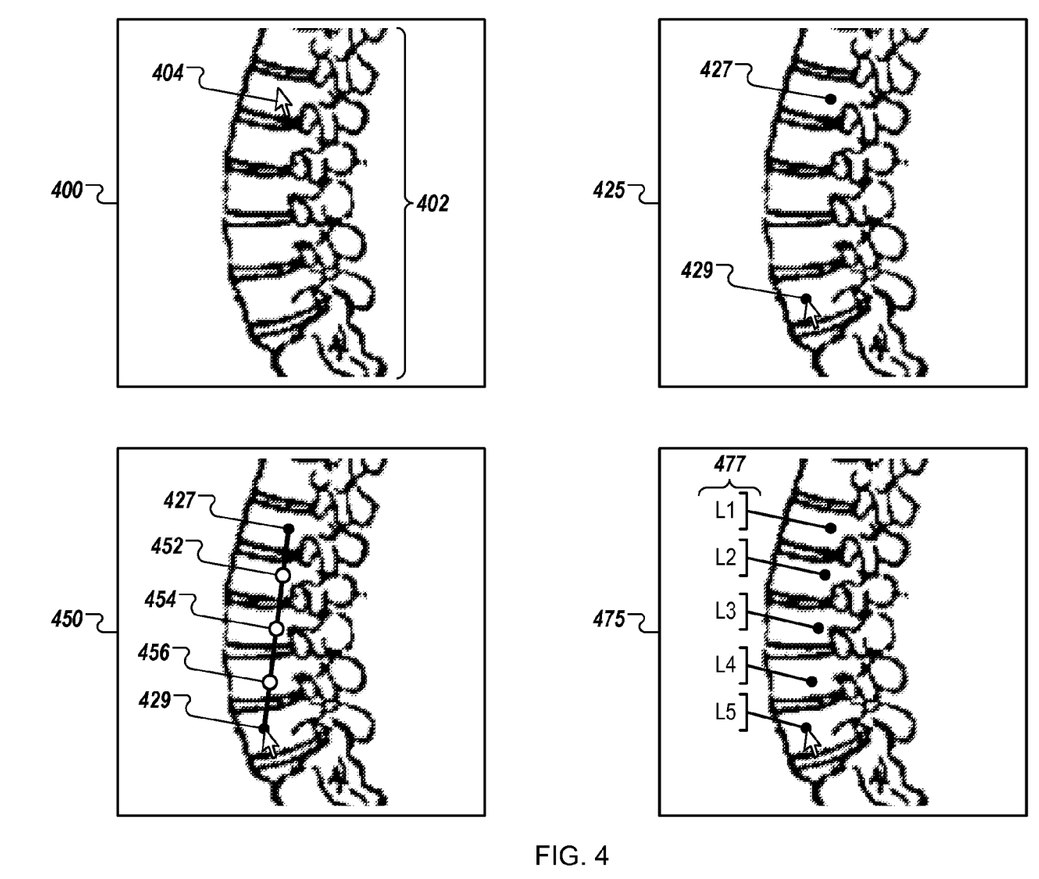
FIG. 4 shows example graphic user interfaces in a system to label anatomy.

FIG. 4 shows example graphic user interfaces 400, 425, 450 and 475 in a system to label anatomy. The graphic user interfaces 400, 425, 450 and 475 here illustrate the display that can be made on a single user terminal for applying labels to an image.

The graphic user interface 400 shows an image of a cross section of lumbar vertebrae 402. A cursor 404 is controlled by user input, such as using a mouse, tablet, keyboard, or trackball. User input can instead or in addition manipulate the image, such as for panning, zooming, and rotation, and translation.

The graphic user interface 425 currently shows two points 427 and 429. The points are created by a user input generated by the user moving the cursor 404 and generating selection input (e.g., mouse click, enter button press, etc). In this example, the points 427 and 429 are located in or around the L1 and L5 vertebrae, respectively, and the point 427 was created first. That is, while looking at the user interface 400 a radiologist can identify the L1 vertebrae and click on it, which creates the point 427, and can then identify the L5 vertebrae and click on it, which creates the point 429.

The graphic user interface 450, in turn, shows three points 452, 454, and 456, having been added between the points 427 and 429. That is, the points 452, 454, and 456 are here added based on the L1 and L5 vertebrae having been identified, so that the intermediate points approximately indicate the vertebrae L3-L5. A line between the points 427 and 429 is shown here, along which the points 452, 454, and 456 are placed. In some examples, the line can be curved, such as along a predetermined path, for example defined by user input. Example user input includes dragging on the line with the cursor or selection of screen options (not shown). In some examples, the points 427, 429, 452, 454, and/or 456 can be moved along the length of the line. In some examples, the line is not calculated and/or shown.

The graphic user interface 475 here shows labels 477 for the L1 through L5 vertebrae. In this example, the labels are displayed in a linear column with lead lines connected to points in the vertebrae labeled. In another example, the labels consist of text located in or around the anatomical feature labeled. In some examples, the text can be altered based on the distance of the camera from the labeled anatomy or labels. For example, the size or transparency of the text can change.

Figure 5:
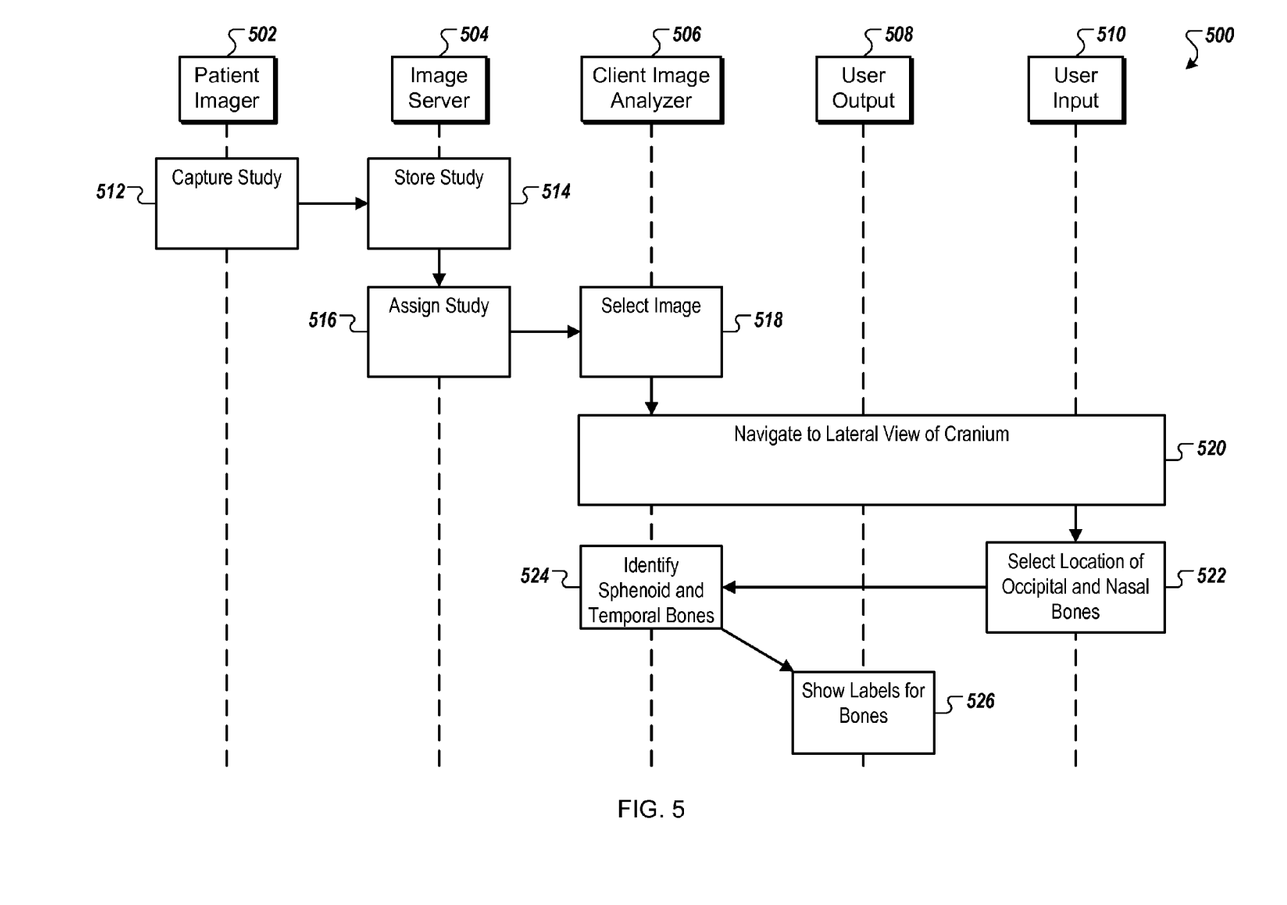
FIG. 5 is a swimlane diagram of an example process for labeling anatomy.

FIG. 5 is a swimlane diagram of an example process 500 for labeling anatomy. In this example, a two-dimensional image of a patient skull is created, and occipital, nasal, sphenoid and temporal bones are labeled. The process 500 can be performed by, for example, a radiology or teleradiology system which captures many different types of medical images and presents the images to a radiologist for analysis.

A patient imager 502 creates a collection of images of a patient, including at least one x-ray image with a lateral view of the patient's skull, in this example. These images are collected into a study (512), which can also include metadata such as patient information, date and time, etc. The patient imager 502 sends the study to an image server 504 that manages radiological studies and assigns the studies to radiologist.

The image server 504 stores the study (514) until such a time that the study, and potentially one or more other studies, are assigned (516) to a radiologist and/or to a client terminal. The client terminal contains a client image analyzer 506 which examines and parses the study for presentation to the user. The parsing can include examination of metadata, grouping images from a study, and organizing the images or study for presentation.

The client image analyzer 506, along with an output 508 to a user, such as on a monitor, and a user input 510, for example made using a keyboard and mouse navigate to an image containing lateral view of the patient's cranium (520). This image is a two-dimensional image that displays the occipital, nasal, sphenoid and temporal bones. The user input 510 selects two points within or near the occipital and nasal bones (510) based on the user's recognition of these features in the image, for example by the user moving a marker with a mouse or pressing arrow keys. The client image analyzer 506 identifies a point within or near each of the sphenoid and temporal bones (524). These points lay along a straight line or predefined curve between the points within or near the occipital and nasal bones, and each a predefined distance along the line or curve, as measured with a ratio or percent of the length.

The output 508 displays the image of the skull including labels for the occipital, nasal, sphenoid, and temporal bones (526) at the related points in the image. In this example, when one or more other two-dimensional images of the skull are displayed by the user output 508, the labels can be displayed in the same location, such as to call out their location in the new image and to assist in the identification of the anatomical features shown.

Figure 6:
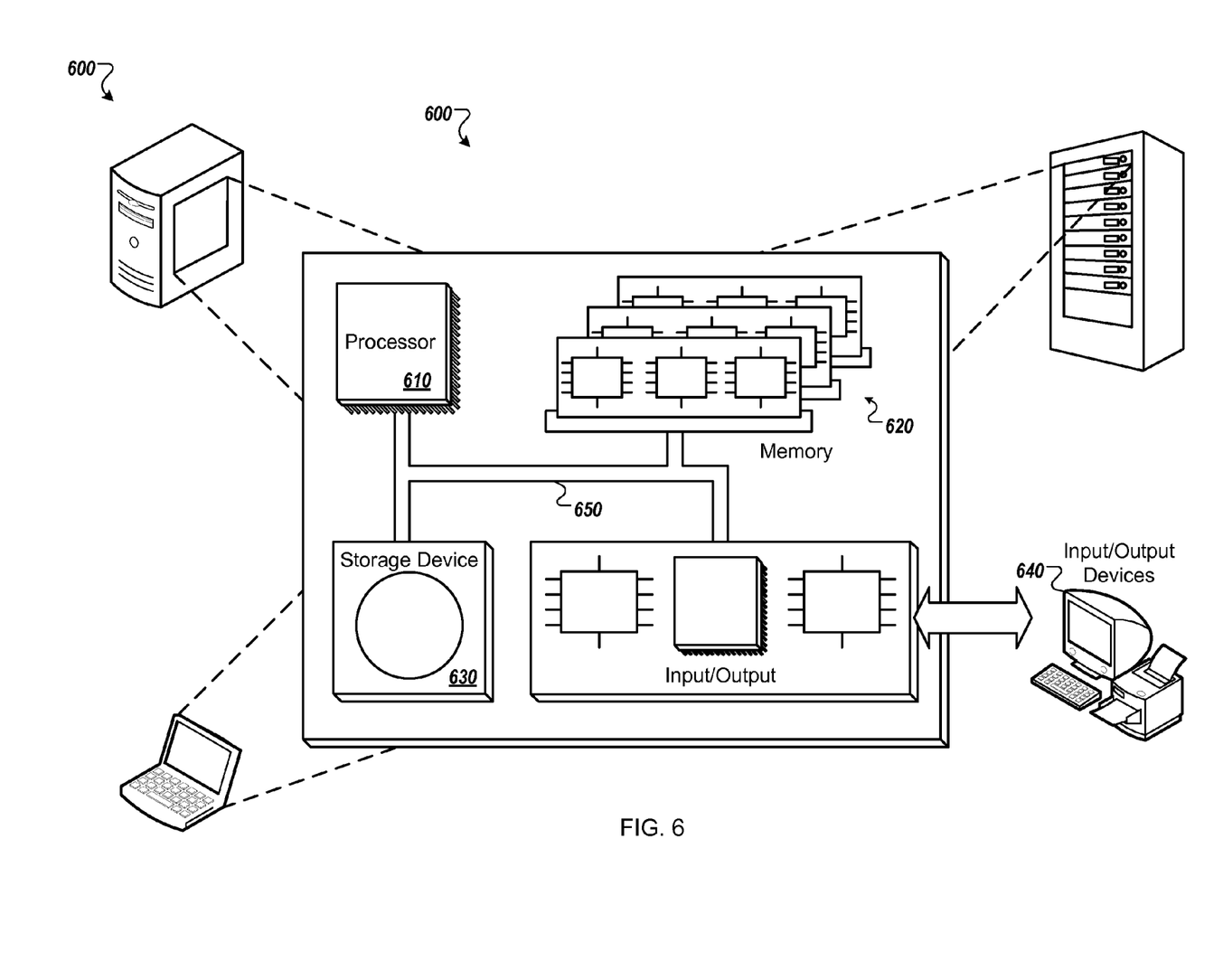
FIG. 6 is a block diagram of a computing system optionally used in connection with computer-implemented methods described in this document.

FIG. 6 is a schematic diagram of a generic computer system 600. The system 600 is optionally used for the operations described in association with any of the computer-implemented methods described previously, according to one implementation. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In one implementation, the memory 620 is a computer-readable medium. In one implementation, the memory 620 is a volatile memory unit. In another implementation, the memory 620 is a non-volatile memory unit.

The storage device 630 is capable of providing mass storage for the system 600. In one implementation, the storage device 630 is a computer-readable medium. In various different implementations, the storage device 630 is optionally a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

In some examples, the features described are implemented in digital electronic circuitry, or in computer hardware, firmware, software, or in combinations of them. The apparatus is optionally implemented in a computer program product tangibly embodied in an information carrier, e.g., in a machine-readable storage device or in a propagated signal, for execution by a programmable processor; and method steps are performed by a programmable processor executing a program of instructions to perform functions of the described implementations by operating on input data and generating output. The described features are optionally implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that are optionally used, directly or indirectly, in a computer to perform a certain activity or bring about a certain result. A computer program is optionally written in any form of programming language, including compiled or interpreted languages, and it is deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory are optionally supplemented by, or incorporated in, ASICs (application-specific integrated circuits).

To provide for interaction with a user, the features in some instances are implemented on a computer having a display device such as a CRT (cathode ray tube) or LCD (liquid crystal display) monitor for displaying information to the user and a keyboard and a pointing device such as a mouse or a trackball by which the user provides input to the computer.

The features are optionally implemented in a computer system that includes a back-end component, such as a data server, or that includes a middleware component, such as an application server or an Internet server, or that includes a front-end component, such as a client computer having a graphical user interface or an Internet browser, or any combination of them. The components of the system are connected by any form or medium of digital data communication such as a communication network. Examples of communication networks include, e.g., a LAN, a WAN, and the computers and networks forming the Internet.

The computer system optionally includes clients and servers. A client and server are generally remote from each other and typically interact through a network, such as the described one. The relationship of client and server arises by virtue of computer programs running on the respective computers and having a client-server relationship to each other.

A number of embodiments have been described. Nevertheless, it will be understood that various modifications are optionally made without departing from the spirit and scope of this disclosure. Accordingly, other embodiments are within the scope of the following claims.

What is claimed is:

1. A computer implemented method for image labeling, the method comprising:
    receiving a medical image containing a visual representation of at least first, second and third anatomical features;
    presenting the medical image to a user at a user terminal;
    receiving, at the user terminal, a first user input indicating a first point in the medical image corresponding to a location of the first anatomical feature;
    receiving, at the user terminal, a second user input indicating a second point in the medical image corresponding to a location of the second anatomical feature;
    determining, using the first and second user inputs, a location of the third anatomical feature in the medical image;
    associating a first label with the first point, a second label with the second point, and a third label with a third point corresponding to a location of the third anatomical feature; and
    displaying, at the user terminal, the medical image with the first label indicating the first point, the second label indicating the second point, and the third label indicating the third point.

2. The method of claim 1, wherein the method further includes:
    displaying, at the user terminal, another medical image than the first medical image, the other image having the first, second and third labels indicating locations of corresponding first, second and third anatomical features, respectively.

3. The method of claim 1, wherein the medical image contains a visual representation of L1, L2, L3, L4 and L5 vertebrae.

4. The method of claim 3, wherein the first anatomical feature is the L1 vertebra, the second anatomical feature is the L5 vertebra, the third anatomical feature is the L2 vertebra, a fourth anatomical feature is the L3 vertebra, and a fifth anatomical feature is the L4 vertebra.

5. The method of claim 4, wherein the method further includes:
   determining a fourth point in the image indicating a location of the fourth anatomical feature;
   determining a fifth point in the image indicating a location of the fifth anatomical feature;
   associating a fourth label with the fourth point and a fifth label with the fifth point; and
   displaying, at the user terminal, the medical image with the first, second, third, fourth and fifth labels.

6. The method of claim 5, wherein the first point, the second point, the third point, the fourth point and the fifth point are coplanar.

7. The method of claim 1, wherein the determination of the location of the third anatomical feature is triggered by receipt of the first and second user inputs, and the medical image and the first, second and third labels are displayed in response to the first and second user inputs.

8. The method of claim 1, wherein the method is performed in a teleradiology environment.

9. A computer program product tangibly embodied in a non-transitory computer-readable storage medium, the computer program product including instructions that, when executed, generate on a display device a graphical user interface for labeling anatomy, the graphical user interface comprising:
   a presentation area for displaying a medical image containing a visual representation of at least first, second and third anatomical features; and
   at least one control for receiving a first user input indicating a first point in the medical image corresponding to a location of the first anatomical feature, and receiving a second user input indicating a second point in the medical image corresponding to a location of the second anatomical feature;
   wherein the presentation area shows a first label at the first point, a second label at the second point, and a third label at a third point corresponding to a location of the third anatomical feature determined using the first and second user inputs.

10. The computer program product of claim 9, wherein appearances of the first label, the second label, and the third label are adjusted in response to user input indicating a change in point of view.

11. The computer program product of claim 9, wherein:
    the presentation area shows an alignment element, the alignment element being one of a line segment and a curve;
    the alignment element touches the first label, the second label and the third label; and
    the alignment element shape is adjustable by user input.

12. The computer program product of claim 9, wherein the control moves in response to user input from one of a keyboard, mouse, trackball, and tablet.

13. A system for image labeling comprising:
    an imaging device configured to capture a medical image containing a visual representation of at least first, second and third anatomical features;
    an image viewer configured to display the medical image; and
    an image analyzer configured:
      to receive a first user input indicating a first point in the medical image corresponding to a location of the first anatomical feature;
      to receive a second user input indicating a first point in the medical image corresponding to a location of the second anatomical feature; and
      to determine a location of the third anatomical feature in the medical image;
    wherein the image viewer displays the medical image, a first label at the first point, a second label at the second point, and a third label at a third point corresponding to a location of the third anatomical feature determined using the first and second user inputs.

14. The system of claim 13, wherein the image viewer:
    displays another medical image than the first medical image, the other image having the first, second and third labels indicating locations of corresponding first, second and third anatomical features, respectively.

15. The system of claim 13, wherein the medical image contains a visual representation of L1, L2, L3, L4 and L5 vertebrae.

16. The system of claim 15, wherein the first anatomical feature is the L1 vertebra, the second anatomical feature is the L5 vertebra, the third anatomical feature is the L2 vertebra, a fourth anatomical feature is the L3 vertebra, and a fifth anatomical feature is the L4 vertebra.

17. The system of claim 16, wherein the image analyzer:
    determines a fourth point in the image indicating a location of the fourth anatomical feature;
    determines a fifth point in the image indicating a location of the fifth anatomical feature;
    associates a fourth label with the fourth point and a fifth label with the fifth point; and
    displays, at the user terminal, the medical image with the first, second, third, fourth and fifth labels.

18. The system of claim 16, wherein the first point, the second point, the third point, the fourth point and the fifth point are coplanar.

19. The system of claim 13, wherein the image analyzer is triggered to determine the location of the third anatomical feature by receipt of the first and second user inputs, and the image viewer displays the medical image and the first, second and third labels in response to the first and second user inputs.

20. The system of claim 13, wherein the system is a teleradiology system.

* * * * *

UNITED STATES PATENT AND TRADEMARK OFFICE
CERTIFICATE OF CORRECTION

PATENT NO. : 8,335,364 B2  
APPLICATION NO. : 12/722233  
DATED : December 18, 2012  
INVENTOR(S) : Osmundson et al.

Page 1 of 1

It is certified that error appears in the above-identified patent and that said Letters Patent is hereby corrected as shown below:

On the face page, in field (57), in "Abstract", in column 2, line 1, before "two", delete "a", therefor In column 1, line 33, before "two", delete "a", therefor Signed and Sealed this  
Second Day of April, 2013

Teresa Stanek Rea  
*Acting Director of the United States Patent and Trademark Office*